(12) United States Patent
Ring et al.

(10) Patent No.: US 6,723,715 B1
(45) Date of Patent: Apr. 20, 2004

(54) 14,15-CYCLOPROPANOSTEROIDS OF THE 19-NORANDROSTANE SERIES, METHOD FOR PRODUCING SAID COMPOUNDS AND PHARMACEUTICAL PREPARATION CONTAINING SAID COMPOUNDS

(75) Inventors: Sven Ring, Jena (DE); Walter Elger, Berlin (DE); Guenter Kaufmann, Jena (DE)

(73) Assignee: Schering AG, Berlin (DE)

( * ) Notice: Subject to any disclaimer, the term of this patent is extended or adjusted under 35 U.S.C. 154(b) by 5 days.

(21) Appl. No.: 10/148,159

(22) PCT Filed: Nov. 21, 2000

(86) PCT No.: PCT/EP00/11553
§ 371 (c)(1),
(2), (4) Date: May 24, 2002

(87) PCT Pub. No.: WO01/42274
PCT Pub. Date: Jun. 14, 2001

(30) Foreign Application Priority Data

Dec. 8, 1999 (DE) .......................... 199 59 697

(51) Int. Cl.$^7$ .................. A61K 31/56; C07J 53/00
(52) U.S. Cl. .................. 514/178; 514/179; 552/510
(58) Field of Search ................ 552/614, 646, 552/648, 510; 514/178, 179

(56) References Cited

FOREIGN PATENT DOCUMENTS

| DE | 198 27 522 A | 12/1999 |
| DE | 198 27 523 A1 | 12/1999 |
| EP | 0 768 316 A | 4/1997 |
| WO | 99/67275 | 12/1999 |

OTHER PUBLICATIONS

P.S. Furth et al J. Enzyme Inhibition, 1990, vol. 4, 131–135.
X.S. Fei et al., J. Chem Soc. Perkin Trans. 1, 1998, 1139–1142.

*Primary Examiner*—Barbara P. Badio
(74) *Attorney, Agent, or Firm*—Michael J. Striker

(57) ABSTRACT

The invention relates to the new 14,15-cyclopropanoandrosteroids of the 19-norandrostane series of the general formula (I)

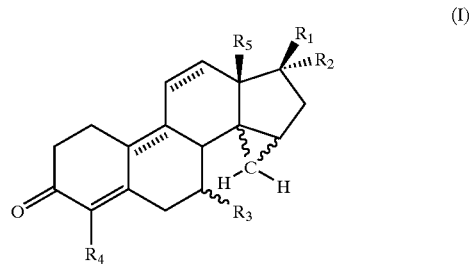

(I)

their synthesis and to pharmaceutical compositions containing these compounds.

The compounds of formula (I) have an interesting, mixed androgen/gestagen profile, the androgenic or gestagenic activity predominating, depending on the substitution.

21 Claims, No Drawings

14, 15-CYCLOPROPANOSTEROIDS OF THE 19-NORANDROSTANE SERIES, METHOD FOR PRODUCING SAID COMPOUNDS AND PHARMACEUTICAL PREPARATION CONTAINING SAID COMPOUNDS

This application is a 371 of PCT/EP00/11553 filed Nov. 21, 2000.

The invention relates to new 14,15-cyclopropanosteroids of the 19-norandrostane series, their synthesis and pharmaceutical preparations containing these compounds.

14,15-Cyclopropanosteroids of the 19-norandrostane series of the following formula

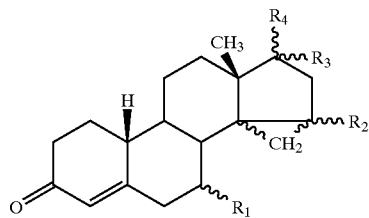

are described in the German application No. 198 27 522.5 (PCT/DE99/01795), which claims a priority earlier than that of the present application, but was published after the latter was filed.

In the above formula, $R_1$ is a hydrogen atom or an alkyl group with 1 to 9 carbon atoms, $R_2$ represents a hydrogen atoms or a methyl group, $R_3$ and $R_4$ independently of one another represent a hydrogen atom, a hydroxy group, an acyloxy group —O—CO—$R_5$, in which $R_5$ represents 1 to 10 carbon atoms, a carbamoyloxy group O—CO—NH$R_6$, in which $R_6$ represents a hydrogen atom, an alkyl group or an acyl group in each case with 1 to 5 carbon atoms, a sulfamoyloxy group —O—SO$_2$—N$R_7R_8$, in which $R_7$ and $R_8$ independently of one another represent a hydrogen atom, an alkyl group with 1 to 5 carbon atoms or, together with the nitrogen atom, represent a pyrrolidino, piperidino or morpholino group, a —CH$_2R_9$ group, in which $R_9$ represents hydroxy group, an alkoxy group, with 1 to 5 carbon atoms, a chlorine or bromine atom, an azide, nitrilo or thiocyano group or a —S$R_{10}$ group, in which $R_{10}$ represents an alkyl group with 1 to 5 carbon atoms, or $R_3$ and $R_4$ together represent an oxo group or $R_3$ and $R_4$, with inclusion of the C-17, form a spirooxirane group or a 2,2-dimethyl-1,3-dioxolane and the 14,15-cyclopropane ring is either in the α a or β position.

The EP 0 768 316 A1 discloses steroids with 14,15-methylene groups, which have progesterone activity and therefore, in combination with at least one suitable estrogen, are suitable for hormonal contraception and menopausal hormone replacement therapy (HRT), as well as for the treatment of endometriosis or gestagen-dependent tumors.

With this state of the art as background, it is an object of the present invention to make available new, unsaturated, 14,15-cyclorano-androstanes.

This objective is accomplished by 14,15-cyclopranoandrostanes of the 19-norandrostane series of the general formula (I)

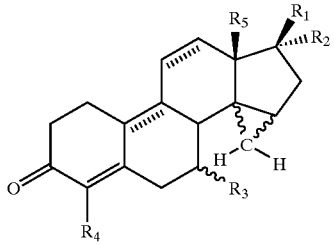

in which $R_1$ is a hydrogen atom, a hydroxy group, $C_{1-10}$-alkyl, $C_{1-10}$-alkyloxy, $C_{1-15}$acyloxy, $C_{4-15}$-aryloxy, $C_{7-15}$-aralkyloxy or a $C_{7-15}$-alkylarylxy group $R_2$ represents a hydrogen atom, a hydroxy group, a $C_{1-10}$ alkyl, $C_{1-10}$ acyl, $C_{1-10}$ acyloxy, $C_{6-15}$ aryl, $C_{7-15}$ aralkyl or $C_{7-15}$ alkylaryl group a —(CH$_2$)$_n$CH$_2$Y group with n=0, 1 or 2 and Y represents a halogen atom, especially a fluorine, chlorine, bromine or iodine atom, a pseudohalogen, especially a cyano, azide or rhodanide group, —(CH$_2$)$_m$—CH=CH(CH$_2$)$_p$—$R_6$ group with m=0, 1, 2 or 3 and p=0, 1 or 2 and $R_5$ represents a hydrogen atom, a $C_{1-10}$ alkyl, $C_{6-15}$ aryl, $C_{7-15}$ aralkyl or $C_{7-15}$ alkylaryl group or a hydroxyl group, a $C_{1-10}$ alkyloxy group or a $C_{1-10}$ acyloxy group, a —(CH$_2$)$_o$C CR$_7$ group with o=0, 1 or 2 and $R_6$ represents a hydrogen atom, a halogen atom, especially a fluorine, chlorine, bromine or iodine atom, a $C_{1-10}$ alkyl, $C_{6-15}$ aryl, $C_{7-15}$ aralkyl, $C_{7-15}$ alkylaryl or $C_{1-10}$ acyl group $R_1$ and $R_2$ together represent a keto, methylene, difluoromethylene group or, with inclusion of the C-17, a spirooxirane or a 2,2-dimethyl-1,3-dioxolane, $R_3$ represents a hydrogen atom or an α or β $C_{1-10}$ alkyl group, $R_4$ represents a halogen atom, especially a fluorine, chlorine or bromine atom, or a pseudohalogen, especially a rhodanide or azide group, or a hydroxyl or perfluoroalkyl group and $R_5$ represents a $C_{1-4}$ alkyl group, there being an α- or β-cyclopropane group between C-14 and C-15, and possibly double bonds in the 9,10 or 11,12 position, with the proviso that, if there are 2 further double bonds in the 9,10 and 11,12 positions or one double bond in the 11,12 position, $R_4$ can be a hydrogen atom in addition to the meanings given above and with the further proviso that, when $R_5$ is a methyl group, $R_4$ can be a hydrogen atom in addition to the meanings given above, as well as their pharmaceutically tolerated salts.

Surprisingly, the compounds of formula (I) show an interesting mixed androgen/gestagen profile, the androgenic or gestagenic activity predominating depending on the substitution.

Within the sense of the invention, pharmaceutically tolerated salts are alkali or alkaline earth salts, especially sodium, potassium or ammonium salts. These salts can be synthesized by standard techniques and methods, which are well known in the art.

Within the sense of the present invention, a "$C_{1-4}$ or $C_{1-10}$ alkyl group" is understood to be a branched or linear alkyl group with 1 to 4 or 1 to 10 carbon atoms. As examples, a methyl, ethyl, n-propyl, i-propyl, n-butyl, i-butyl or t-butyl, n-pentyl, i-pentyl, n-hexyl, 2-methylpentyl, 3-methylpentyl, 2,2-dimethylbutyl or 2,3-dimethylbutyl group are mentioned.

Within the sense of the present invention, the concept of "$C_{1-10}$ alkoxy group" is understood to include cyclic or acyclic groups, the alkyl portion of which contains 1 to 10 carbon atoms. "Cyclic groups" are understood to include also heterocyclic groups, which may have 1 or 2 hetero atoms in the ring, which may be selected from a nitrogen atom, an oxygen atom and a sulfur atom. A methoxy group, an ethoxy group or an n- or iso-propoxy group or an iso- or t-butoxy, a 1'-methoxy-cyclopentoxy or a tetrahydropyranyloxy group are examples.

In the sense of the present application, the concept of $C_{1-10}$ or $C_{1-15}$ acyl or acyloxy group" is understood to be a group with 1 to 10 or 1 to 15 carbon atoms of the linear or branched alkane carboxylic acids, such as formic acid, acetic acid, propionic acid, butyric acid, iso-butyric acid, heptanoic acid or undecanoic acid.

Within the sense of the present application, the concept of a "$C_{6-15}$ aryl group" is understood to include a substituted or unsubstituted aryl group with 6 to 15 carbon atoms, such as a phenyl group, a substituted phenyl group, such as a halogenated phenyl group or a nitrophenyl group, or a naphthyl group.

Within the sense of the present application, the concept of a "$C_{4-15}$ aryloxy group" is understood to include a carbocyclic or heterocyclic group with 4 to 15 carbon atoms. Examples are a benzoyloxy group, a 1- or 2-naphthinyloxy group, a 2- or 3-furanyloxy group, a 2- or 3-thienyl group and a 2-, 3- or 4-pyridinyloxy group.

Within the sense of the present application, the concept of a "$C_{7-15}$ alkylaryl group" is understood to include an aryl group, which is substituted by an alkyl group, the two group together of 7 to 15 carbon atoms. The aryl group may have additional substituents, such as a halogen atom. Examples are a toluenyl group (methylphenyl group), a halogenated toluenyl group, an ethylphenyl group, a dimethylphenyl group or a trimethylphenyl group.

Within the sense of the present application, the concept of a "$C_{7-15}$ alkylaryloxy group" is understood to be a "$C_{7-15}$ aralkyl group", such as a 3- or a 4-methylphenyloxy group, which is extended by an oxygen atom.

Within the sense of the present application, the concept of a "$C_{7-15}$ aralkyl group" is understood to include an alkyl group, which is substituted by an aryl group, the two groups together having 7 to 15 carbon atoms. The aryl group may have further substituents, such as a halogen atom. Examples are a free or an aromatically substituted benzyl groups, such as a benzyl group or a halogenated benzyl group.

Within the sense of the present application, the concept of "$C_{7-15}$ aralkyloxy group" is understood to include "$C_{7-15}$ aralkyl groups", which has been extended by an oxygen atom, such as a benzyloxy group.

Within the sense of the present application, the concept of "halogen" comprises a fluorine, bromine or iodine atom.

Within the sense of the present application, the concept of "pseudohalogen" comprises a cyanate, rhodanide, cyan or azide group.

Within the sense of the present application, the concept of "perfluoroalkyl group" comprises branched or linear fluoroalkyl groups with 1 to 3 carbon atoms, such as a trifluoromethyl, pentafluoroethyl, heptafluoro-n-propyl or heptafluoro-i-propyl group.

$R_1$ preferably represents a hydroxy or $C_{1-11}$ acyloxy group, especially a formyloxy, acetyloxy, propionyloxy, n-butyryloxy, iso-butyryloxy, heptanyloxy or undecanyloxy group.

If $R_2$ represents a —$(CH_2)_nCH_2Y$ group, n preferably is 1 and Y preferably represents a fluorine atom or a cyano or rhodanide group. If $R_2$ is a —$(CH_2)_m$—CH=CH$(CH_2)_p$—$R_6$ group, n preferably is 1 and $R_6$ preferably represents a methyl or ethyl group or a methoxy or ethoxy group.

If $R_2$ represents a —$(CH_2)_oC$ C$R_7$ group, o preferably is 1 and $R_7$ preferably represents a fluorine atom or a methyl or ethyl group.

$R_2$ especially represents a hydrogen atom or a $C_{1-6}$ alkyl group, especially a methyl or ethyl group.

$R_3$ preferably represents a $C_{1-4}$ alkyl group, a methyl group being especially preferred.

$R_4$ preferably represents a fluorine, chlorine or bromine atom or a trifluoromethyl or hydroxy group, and $R_5$ preferably represents a methyl or ethyl group.

The most preferred compounds are the following 1) 4-chloro-17β-hydroxy-14α,15α-methylene-estr-4-ene-3-one
2) 4-chloro-17α-hydroxy-14α,15α-methylene-estr-4-ene-3-one
3) 4-chloro-17β-hydroxy-14β,15β-methylene-estr-4-ene-3-one
4) 4-chloro-17α-hydroxy-14β,15β-methylene-estr-4-ene-3-one
5) 4-bromo-17β-hydroxy-14α,15α-methylene-estr-4-ene-3-one
6) 4-bromo-17α-hydroxy-14α,15α-methylene-estr-4-ene-3-one
7) 4-bromo-17β-hydroxy-14β,15β-methylene-estr-4-ene-3-one
8) 4-bromo-17α-hydroxy-14β,15β-methylene-estr-4-ene-3-one
9) 4-fluoro-17β-hydroxy-14α,15α-methylene-estr-4-ene-3-one
10) 4-fluoro-17α-hydroxy-14α,15α-methylene-estr-4-ene-3-one
11) 4-fluoro-17β-hydroxy-14β,15β-methylene-estr-4-ene-3-one
12) 4-fluoro-17α-hydroxy-14β,15β-methylene-estr-4-ene-3-one
13) 4,17β-dihydroxy-14α,15α-methylene-estr-4-ene-3-one
14) 4,17α-dihydroxy-14α,15α-methylene-estr-4-ene-3-one
15) 4,17β-dihydroxy-14β,15β-methylene-estr-4-ene-3-one
16) 4,17α-dihydroxy-14β,15β-methylene-estr-4-ene-3-one
17) 4-trifluoromethyl-17β-hydroxy-14α,15α-methylene-estr-4-ene-3-one
18) 4-trifluoromethyl-17α-hydroxy-14α,15α-methylene-estr-4-ene-3-one
19) 4-trifluoromethyl-17β-hydroxy-14β,15β-methylene-estr-4-ene-3-one
20) 4-trifluoromethyl-17α-hydroxy-14β,15β-methylene-estr-4-ene-3-one
22) 17β-hydroxy-14α,15α-methylene-estra-4,9,11-triene-3-one
23) 17α-hydroxy-14α,15α-methylene-estra-4,9,11-triene-3-one
24) 17β-hydroxy-14α,15α-methylene-estra-4,9,11-triene-3-one
25) 17β-hydroxy-14β,15β-methylene-estra-4,9,11-triene-3-one and 26) 17α-hydroxy-14β,15β-methylene-estra-4,9,11-triene-3-one The inventive compounds of formula (I) can be synthesized in that, in 14, 15-cyclopropanosteriods of the general formula (II)

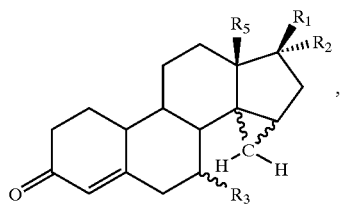

(II)

in which $R_1$, $R_2$, $R_3$ and $R_5$ have the meaning given above, the 4, 5 double bond is epoxidized with hydrogen peroxide under alkaline conditions and the resulting epoxide mixture is treated in a suitable solvent with acids having the general formula $HR_8$, $R_8$ being a halogen atom or a pseudohalogen atom, or reacted with catalytic amounts of a mineral acid and the 4-bromo compound of the general formula (I), obtained above, is reacted with methyl 2,2-difluoro-2-(fluorosulfonyl) acetate in dimethylformamide in the presence of CuI.

The synthesis of compounds of formula (II) is carried out by known methods or described in the German application No. 198 27 522.6 (PCT/DE99/01795). In the application referred to, the introduction of the groups, which occur there and are analogous to the $R_1$, $R_2$, $R_3$ and $R_5$ groups claimed here, is described.

Moreover, corresponding 4-bromo compounds can also be synthesized by the addition of bromine by means of bromine, N-bromosuccinimide or N-bromoacetamide to compounds of the general formula (II) in a mixture of acetic acid and ether in the presence of a proton acceptor, such as collidine (X. S. Fei et. al., J. Chem. Soc. Perkin Trans. 1, 1998, 1139–1142).

4-Trifluoromethyl compounds of the general formula (I) can be obtained by reacting the 4-bromo compounds of the general formula (I), obtained above, with methyl 2,2-difluoro-2-(fluorosulfonyl)-acetate in dimethylformamide in the presence of CuI (X. S. Fei et. al., J. Chem. Soc. Perkin Trans. 1, 1998, 1139–1142). 4-Hydroxy compounds are obtained by reacting the epoxide mixture, given above, with catalytic amounts of mineral acid, such as sulfuric acid (P. S. Furth et. al., J. Enzyme Inhibition, 1990, v. 4, 131–135). Compounds of the general formula (I), which contain a 4,9,11-triene structure, can be transformed from compounds of the general formula (III)

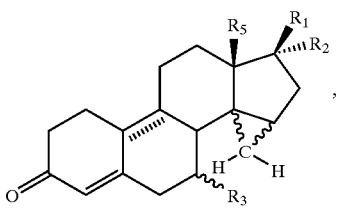

(III)

in which $R_1$, $R_2$, $R_3$ and $R_5$ have the meaning given above (synthesized, for example, according to the method of EP 0 768 316 A1) by methods known from the literature into compounds with a 4,9,11-triene structure of the general formula (I). Accordingly, compounds such as those of the general formula (III) can be ketalized in the 3 position, a 5(10),9(11) diene being formed. After careful hydrolysis of the ketal group of, a 5(10),9(11)-diene-3-one is then obtained, which can easily be dehydrogenated with dichlorodicyanobenzoquinone to the desired compounds of the general formula (I) (according to the method of M. Heller, R. H. Lenhard, S. Bernstein, Steroids 1967, pp. 211–217). In addition, it is possible to convert the 5(10),9(11)-diene-3-one into the 11β-hydroperoxide. After the 11β-hydroperoxide is reduced to the 11β-hydroxy compound, the hydroxy group can be split off under acidic conditions with the formation of the desired compounds of the general formula (I) by the method of L. Nedelec, V. Torelli, G. Costerousse, V. Delaroff, Bull. Soc. Chim., 1977, pages 670–675).

Pharmaceutical drugs, for the oral, rectal, subcutaneous, intravenous oral intramuscular application which, together with the conventional vehicles and diluents, contain at least one compound of the general formula (I) and/or their acid addition salts as active ingredient, are also an object of the present invention.

Pharmaceutical preparations of the invention are produced with the usual solid or liquid vehicles and/or diluents and the inactive ingredients usually used in accordance with the desired type of application in a suitable dosage and by known procedures. In the case of a preferred oral form of administration, preferably tablets, film-coated tablets, coated tablets, capsules, pills, powders, solutions or suspensions are prepared also in sustained release form. In addition, parenteral forms of medicinal drugs, such as injection solutions or suspensions, can also be considered.

Medicinal drug forms as tablets can be obtained for example by mixing the active ingredient with the known inert materials, such as dextrose, sugar, sorbitol, mannitol, polyvinylpyrrolidone, disintegrants such as corn starch or alginic acid, binders such as starch or gelatin, lubricants such as magnesium stearate or talc and/or agents, which can achieve a sustained release effect, such as carboxypolymethylene, carboxymethylcellulose, cellulose acetate phthalate or polyvinyl acetate. The tablets may also consist of several layers.

Similarly, coated tablets can be prepared by coating cores, prepared similarly to the tablets, with agents used in conventional tablet coatings, such as polyvinylpyrrolidone or shellac, gum arabic, talc, titanium dioxide or sugar. The tablet coating may consist of several layers, the inert materials, named above, for example being used.

To improve the taste, the solutions or suspensions with the inventive active ingredients can be mixed with materials such as saccharin, cyclamate or sugar and/or with aromatic and flavoring materials such as vanillin or orange extract. Moreover, they may be mixed with suspending agents, such as sodium carboxymethylcellulose, or preservatives, such as p-hydroxybenzoic acid.

Capsules can be prepared by mixing medicinal drugs with vehicles, such as lactose or sorbitol, which are then brought into the capsules.

Suppositories are prepared preferably by mixing active ingredients with suitable vehicles, such as neutral fats or polyethylene glycols or their derivatives.

The pharmaceutical forms of preparations furthermore can be percutaneous forms, such as transdermal therapeutic systems (TTS) or gels, sprays or ointments or intranasal forms, such as nose sprays or oral nose drops.

The inventive 14,15-cyclopropanosteroids of the 19-norandrostane series of the general formula (I) are compounds with hormonal (gestagenic and/or androgenic) activity.

For example, 4-chloro-17β-hydroxy-14α,14α-methylene-estr-4-ene-3-one binds to the extent of 98% to the androgen receptor to (R 1881=100%) and to the extent of 5.5% to the progesterone receptor (progesterone=100%). On the other hand, 17β-hydroxy-14α,15α-methylene-estra-4,9,11-triene-3-one binds to the extent of 58% to the androgen receptor and to the extent of 36% to the progesterone receptor. These test results open up various possibilities for the inventive compounds of the general formula (I) for fertility control in men and women, hormone replacement therapy in men and women or the treatment of hormonally induced diseases in men and women, such as endometriosis, breast cancer or hypogonadism.

The following examples are intended to explain the invention in greater detail without limiting it.

EXAMPLES

Example 1

4-Substituted Compounds From 4,5-Epoxides
Step 1: Synthesis of 4,5 Epoxides
4ξ,5ξ-Epoxy-17β-hydroxy-14α,15α-methylene-estran-3-one 17β-Hydroxy-14α,15α-methylene-estr-4-ene-3-one (2 g) was dissolved in 50 ml of methanol and treated at 10° C. with hydrogen peroxide solution (35%). While stirring, 5 ml of a 10 sodium hydroxide solution was added and the stirring was continued for 3 hours. The reaction solution is mixed with 50 ml of dichloromethane and 25 ml of water and the organic phase is removed, washed with semi-concentrated thiosulfate solution, dried and evaporated to dryness. The residue obtained consists of a mixture of 4α,5α- and 4β,5β epoxides and is used in the subsequent step without further purification.

Step 2: 4-Substituted Compounds
4-Chloro-17β-hydroxy-14α,15α-methylene-estr-4-ene-3-one The epoxide mixture of step 1 (2 g) is dissolved in 200 ml of acetone and treated at 5° C. with 12 ml of concentrated hydrochloric acid. After 2 house, the mixture is neutralized with sodium carbonate solution and the acetone is removed. The residue is extracted with dichloromethane. The organic extracts are dried and concentrated, After crystallization from ethanol, 4-chloro-17β-hydroxy-14α,15α-methylenestr-4-ene-3-one is obtained.

$^1$H-NMR: 0.19 (2H, m, $CH_2$-bridge), 1.02 (3H, s, H-18), 3.50 (1H, dd, J=9.4, 6.6 Hz, H-17).

Example 2

4-Bromo-17β-hydroxy-14α,15α-methylene-estr-4-ene-3-one

In a manner, analogous to 4-chloro-17β-hydroxy-14α,15α-methylenestr-4-ene-3-one, 4-bromo-17β-hydroxy-14α,15α-methylenestr-4-ene-3-one is obtained if 48% hydrobromic acid is used instead of hydrochloric acid.

$^1$H-NMR: 0.22 (2H, m, $CH_2$-bridge), 1.08 (3H, s, H-18), 3.48 (1H, dd, H-17).

Example 3

4,17β-Dihydroxy-14α,15α-methylene-estr-4-ene-3-one

The epoxide mixture of step 1 (2 g) is dissolved in 20 ml of acetic acid, which contains 2% by volume of concentrated sulfuric acid. The solution is allowed to stand for 3 days at 10° C. After that, it is mixed with 200 ml of ethyl acetate and neutralized with sodium carbonate solution. The organic phase is dried and concentrated. The residue is dissolved in 50 ml of methanol, treated with 2 g of potassium hydroxide, refluxed for 1 hour, cooled, and neutralized with 50 ml acetic acid and poured into 500 mL of water. The crystals of 4,17β-dihydroxy-14α,15α-methylenestr-4-ene-3-one obtained are filtered off with section.

$^1$H-NMR: 0.20 (2H, m, $CH_2$-bridge), 1.10 (3H, s, H-18), 3.50 (1H, m, H-17), 6.10 (1H, s, 4-OH).

Example 4

4-Trifluoromethyl-17β-hydroxy-14α,15α-methylene-estr-4-ene-3-one

4-Bromo-17β-hydroxy-14α,15α-methylenestr-4-en-3-one is dissolved in 100 ml of dimethylformamide and stirred with 0.5 g of CuI as well as 2 ml of methyl 2,2-difluoro-2-(fluorosulfonyl)-acetate for 15 hours at 80° C. After the product is worked up and purified by chromatography, 4-trifluoromethyl-17β-hydroxy-14α,15α-methylene-estr-4-ene-3-one is obtained.

$^1$H-NMR: 0.22 (2H, m, $CH_2$-bridge), 1.06 (3H, s, H-18), 3.50 (1H, dd, J=9.4, 6.6 Hz, H-17). $^{19}$F-NMR: −57.2 (3F, s, 4-$F_3$C).

Example 5

Synthesis of 4,9,11-Trienes 17β-Hydroxy-14α,15α-methylene-estr-4,9,11-triene-3-one 17β-Hydroxy-14α,15α-methylene-estr-4,9-triene-3-one (4 g) is dissolved in 40 ml of methanol and mixed with 16 ml of trimethyl orthoformate and 50 mg of p-toluenesulfonic acid. Stirring at 25° C. is continued for 1.5 hours, after which the pH is adjusted to a value of 9 with 1N methanolic potassium hydroxide solution, 50 ml of water are added and the methanol is distilled off under vacuum. The precipitated substance is filtered off with suction and washed with water. The 3,3-dimethoxy-14α,15α-methylenestr-5(10),9,11-diene-17β-ol (4.3 g) obtained is dissolved in 50 ml of 80% aqueous acetone and 1.6 mL of 20% sulfuric acid are added dropwise. After the stirring has been continued for 1.5 hours at room temperature, 2.5 ml of triethylamine 200 ml of water are added, a solid product precipitating. The latter is filtered off with suction and washed with water, 17β-hydroxy-14α,15α-methylenestr-5(10)-9(11)-diene-3-one (3.8 g) being obtained. The latter (3.8 g), in 18 ml of dioxane, is stirred for 3.5 hours at 40° C. with 6 g of dichloro-dicyanobenzoquinone and then allowed to cool. The precipitate is filtered off and washed with dioxane and the filtrates are concentrated to dryness. The residue is chromatographed on silica gel, 17β-hydroxy-14α,15α-methylene-estr-4,9,11-triene-3-one being obtained.

$^1$H-NMR: 0.18 (1H, m, $CH_2$-bridge), 0.27 (1H, m, $CH_2$-bridge), 1.15 (3H, s, H-18), 3.77 (1H, dd, I=9.0, 7.0 Hz, H-17), 6.42 and 6.51 (2H, 2d, J=9.6 Hz, H-11, H-12).

What is claimed is:
1. 14,15-cyclopranoandrostanes of the 19-norandrostane series of the formula (I)

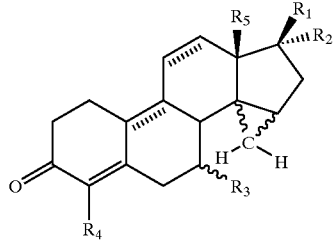

(I)

wherein $R_1$ is a hydrogen atom, a hydroxy group, $C_{1-10}$-alkyl, a $C_{1-10}$-alkyloxy, a $C_{1-15}$ acyloxy, a $C_{4-15}$-aryloxy, a $C_{7-15}$-aralkyloxy or a $C_{7-15}$-alkylaryloxy group;

$R_2$ represents a hydrogen atom, a hydroxy group, a $C_{1-10}$ alkyl group, a $C_{1-10}$ acyl group, a $C_{1-10}$ acyloxy group, a $C_{6-15}$ aryl group, a $C_{7-15}$ aralkyl group, a $C_{7-15}$ alkylaryl group, a —$(CH_2)_nCH_2Y$ group with n=0, 1 or 2 and Y representing a halogen atom or a pseudohalogen; a $(CH2)_mCH=CH(CH_2)_pR_6$ group with m=0,1, 2 or 3 and p=0, 1 or 2 and $R_6$ representing a hydrogen atom, a $C_{1-10}$-alkyl group, a $C_{6-15}$ aryl group, a $C_{7-15}$ aralkyl group, a $C_{7-15}$ alkylaryl group, a hydroxyl group, a $C_{1-10}$ alkyloxy group, a $C_{1-10}$ acyloxy group; a —$(CH_2)_oC\equiv CR_7$ group with o=0, 1 or 2 and $R_7$ representing a hydrogen atom, a halogen atom, a $C_{1-10}$ alkyl group, a $C_{6-15}$ aryl group, a $C_{7-15}$ aralkyl group, a $C_{7-15}$ alkylaryl group or a $C_{1-10}$ acyl group; or $R_1$ and $R_2$ together represent a keto group, a methylene group, a difluoromethylene group or, with inclusion of C-17, a spirooxirane or a 2,2-dimethyl-1,3-dioxolane;

$R_3$ represents a hydrogen atom or an $\alpha$-$C_{1-10}$ alkyl group or $\beta$-$C_{1-10}$ alkyl group;

$R_4$ represents a halogen atom, a pseudohalogen, a hydroxy group or a perfluoroalkyl group;

$R_5$ represents a $C_{1-4}$ alkyl group, wherein an $\alpha$-cyclopropane or a $\beta$-cyclopropane group is between C-14 and C-15; and wherein optionally a 9,10-double bond is present and optionally an 11,12-double bond is present, with the proviso that, if both the 9,10-double bond and the 11,12-double bond are present or if only the 11,12-double bond is present, then $R_4$ can be a hydrogen atom in addition to said halogen atom, said pseudohalogen, said hydroxy group or said perfluoroalkyl group; and with the further proviso that, if $R_5$ is a methyl group, then $R_4$ can be a hydrogen atom in addition to said halogen atom, said pseudohalogen, said hydroxy group or said perfluoroalkyl group;

or pharmaceutically tolerated salts thereof.

2. The 14,15-cyclopranoandrostanes as defined in claim 1, wherein Y is a fluorine atom, a chlorine atom, a bromine atom, an iodine atom, a cyano group, an azide group or a rhodanide group.

3. The 14,15-cyclopranoandrostanes as defined in claim 1, wherein $R_7$ is a fluorine atom, a chlorine atom, a bromine atom or an iodine atom.

4. The 14,15-cyclopranoandrostanes as defined in claim 1, wherein $R_4$ is a fluorine atom, a chlorine atom, a bromine atom, an azide group or a rhodanide group.

5. The 14,15-cyclopranoandrostanes as defined in claim 1, wherein said $R_1$ is a hydroxy group or an acyloxy group.

6. The 14,15-cyclopranoandrostanes as defined in claim 5, wherein said acyloxy group is a formyloxy, an acetyloxy, a propionyloxy, a n-butyryloxy, an isobutyryloxy, a heptanyloxy or an undecanyloxy group.

7. The 14,15-cyclopranoandrostanes as defined in claim 1, wherein $R_2$ is a hydrogen atom or an alkyl group.

8. The 14,15-cyclopranoandrostanes as defined in claim 7, wherein said alkyl group is a methyl group or an ethyl group.

9. The 14,15-cyclopranoandrostanes as defined in claim 1, wherein $R_3$ is a methyl group.

10. The 14,15-cyclopranoandrostanes as defined in claim 1, wherein $R_4$ is a fluorine atom, a chlorine atom, a bromine atom, a hydroxy group or a trifluoromethyl group.

11. The 14,15-cyclopranoandrostanes as defined in claim 1, wherein $R_5$ is a methyl group or an ethyl group.

12. A 14,15-cyclopranoandrostane selected from the group consisting of 4-chloro-17β-hydroxy-14α,15α-methylene-estr-4-ene-3-one, 4-chloro-17α-hydroxy-14α,15α-methylene-estr-4-ene-3-one, 4-chloro-17β-hydroxy-14β,15β-methylene-estr-4-ene-3-one, 4-chloro-17α-hydroxy-14β,15β-methylene-estr-4-ene-3-one, 4-bromo-17β-hydroxy-14α,15α-methylene-estr-4-ene-3-one, 4-bromo-17α-hydroxy-14α,15α-methylene-estr-4-ene-3-one, 4-bromo-17β-hydroxy-14β,15β-methylene-estr-4-ene-3-one, 4-bromo-17α-hydroxy-14β,15β-methylene-estr-4-ene-3-one, 4-fluoro-17β-hydroxy-14α,15α-methylene-estr-4-ene-3-one, 4-fluoro-17α-hydroxy-14α,15α-methylene-estr-4-ene-3-one, 4-fluoro-17β-hydroxy-14β,15β-methylene-estr-4-ene-3-one, 4-fluoro-17α-hydroxy-14β,15β-methylene-estr-4-ene-3-one, 4,17β-dihydroxy-14α,15α-methylene-estr-4-ene-3-one, 4,17α-dihydroxy-14α,15α-methylene-estr-4-ene-3-one, 4,17β-dihydroxy-14β,15β-methylene-estr-4-ene-3-one, 4,17α-dihydroxy-14β,15β-methylene-estr-4-ene-3-one, 4-trifluoromethyl-17β-hydroxy-14α,15α-methylene-estr-4-ene-3-one, 4-trifluoromethyl-17α-hydroxy-14α,15α-methylene-estr-4-ene-3-one, 4-trifluoromethyl-17β-hydroxy-14β,15β-methylene-estr-4-ene-3-one, 4-trifluoromethyl-17α-hydroxy-14β,15β-methylene-estr-4-ene-3-one, 17β-hydroxy-14α,15α-methylene-estra-4,9,11-triene-3-one, 17α-hydroxy-14α,15α-methylene-estra-4,9,11-triene-3-one, 17β-hydroxy-14β,15β-methylene-estra-4,9,11-triene-3-one and 17α-hydroxy-14β,15β-methylene-estra-4,9,11-triene-3-one.

13. A method for the synthesis of the 14,15-cyclopranoandrosteriods defined in claim 1, wherein, in 14,15-cyclopropanosteroids of the formula (II):

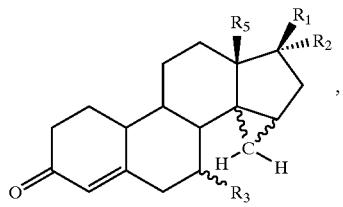

(II)

in which $R_1$, $R_2$, $R_3$, $R_5$ are as defined in claim 1, the 4,5 double bond is epoxidized with hydrogen peroxide under alkaline conditions and the resulting epoxide mixture is treated in a solvent with acids of the formula $HR_8$, $R_8$ being a halogen atom or a pseudohalogen atom, or reacted with catalytic amounts of a mineral acid, and the compound of the formula (I), as defined in claim 1, obtained above, is reacted with methyl 2,2-difluoro-2-(fluorosulfonyl) acetate in dimethylformamide in the presence of CuI.

14. The method as defined in claim 13, wherein said halogen atom is a fluorine, chlorine or bromine atom.

15. The method as defined in claim 13, wherein said pseudohalogen is an azide or a rhodanide group.

16. A method for the synthesis of the 14,15-cyclopranoandrostanes defined in claim 1, wherein, compounds of the formula (III):

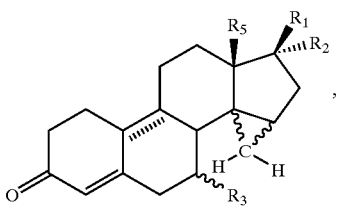

(III)

in which $R_1$, $R_2$, $R_3$ and $R_5$ are as defined in claim 1, are converted into the 14,15-cyclopranoandrostanes of the formula (I) with a 4,9,11-triene structure by ketalizing the compounds of the formula (III), hydrolyzing the ketal group of the thereby formed 5(10),9(11)-diene and reacting the 5(10),9(11)-diene-3-one obtained thereby with dichlorodicyanobenzoquinone.

17. A pharmaceutical composition containing at least one of the 14,15-cyclopranoandrostanes defined in claim 1 and at least one additional ingredient selected from the group consisting of pharmaceutically tolerated inactive materials and vehicles.

18. A method of hormone replacement therapy in a man or woman in need of said therapy, said method comprising administering to said man or said woman an effective amount of at least one of the 14,15-cyclopranoandrostanes as defined in claim 1 for said hormone replacement therapy.

19. A method of controlling fertility of a human being, said method comprising administering to said human being an effective amount of at least one of the 14,15-cyclopranoandrostanes as defined in claim 1 for controlling said fertility.

20. A method of treating a hormone-induced disease suffered by a man or a woman, said method comprising administering to said man or said woman an effective amount of at least one of the 14,15-cyclopranoandrostanes as defined in claim 1 for treating said hormone-induced disease.

21. The method as defined in claim 20, wherein said hormone-induced disease is endometriosis, breast cancer or hypogonadism.

* * * * *